United States Patent [19]

Joh

[11] Patent Number: 4,578,077
[45] Date of Patent: Mar. 25, 1986

[54] BLOOD PUMP APPLICABLE TO AN ARTIFICAL HEART

[75] Inventor: Yasushi Joh, Yokohama, Japan

[73] Assignee: Nippon Zeon Co., Ltd., Tokyo, Japan

[21] Appl. No.: 319,718

[22] Filed: Nov. 9, 1981

[30] Foreign Application Priority Data

Nov. 10, 1980 [JP] Japan ................................ 55-157942

[51] Int. Cl.$^4$ ............................................. A61F 1/00
[52] U.S. Cl. ........................................ 623/3; 128/1 R
[58] Field of Search ...................... 128/1 R; 3/1.5, 1.7

[56] References Cited

U.S. PATENT DOCUMENTS 3,208,448 9/1965 Woodward .............................. 3/1.7
3,327,322 6/1967 Norton ..................................... 3/1.7

OTHER PUBLICATIONS

Szycher, et al., "Select. of Mater. for VAP Devel. & Fabric.", vol. XXIII, Trans. Am. Soc. Artif. Inter. Organ., 1977, 116–126.

Primary Examiner—Richard J. Apley
Assistant Examiner—David J. Isabella
Attorney, Agent, or Firm—Armstrong, Nikaido, Marmelstein & Kubovcik

[57] ABSTRACT

A blood pump to be utilized as an artificial heart, comprises a housing provided with a port for introducing and discharging fluid, a cover portion for closing the housing tightly, a sac portion defining a blood chamber with the relatively flat or oval shape arranged in the housing, an inlet and outlet conduit portions for the blood provided with a check valve respectively and integrally formed on the cover so as to communicate with the blood chamber, characterized in that, when the blood chamber is compressed, the initial contact point from the opposite inner surfaces of the sac is regulated to locate in the area defined by a circle, the center of which is on the central axis of the wider side of the sac and in the height range between 0.2L and 0.45L from the bottom of the sac and the radius of which is 0.15D, where L is the whole height of the sac, D is the maximum width of the sac and the wider side is defined by the side projected to the vertical plane including the maximum width D of the sac.

24 Claims, 28 Drawing Figures

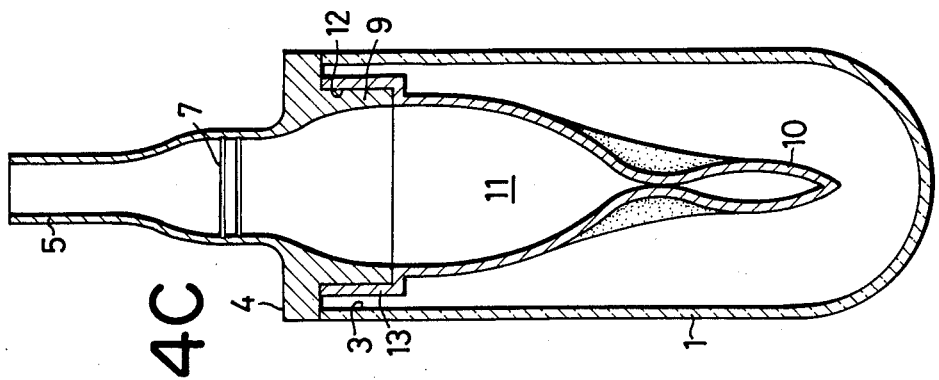
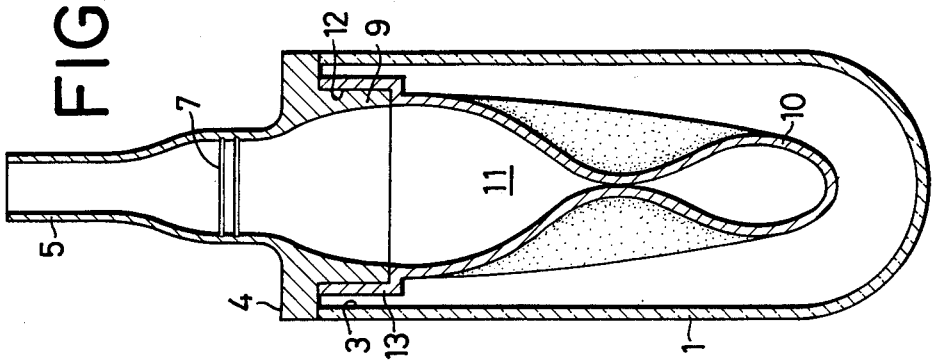
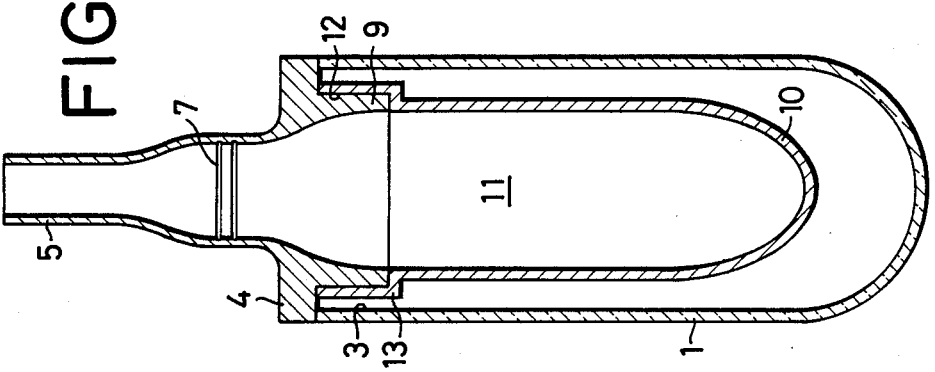

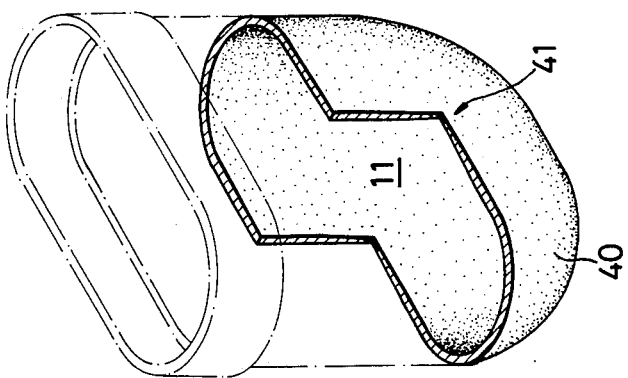
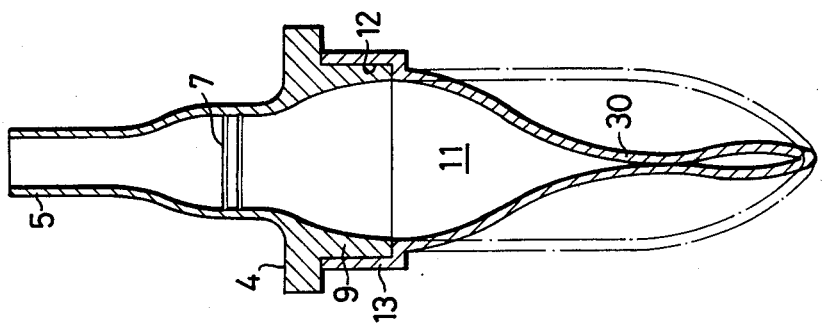
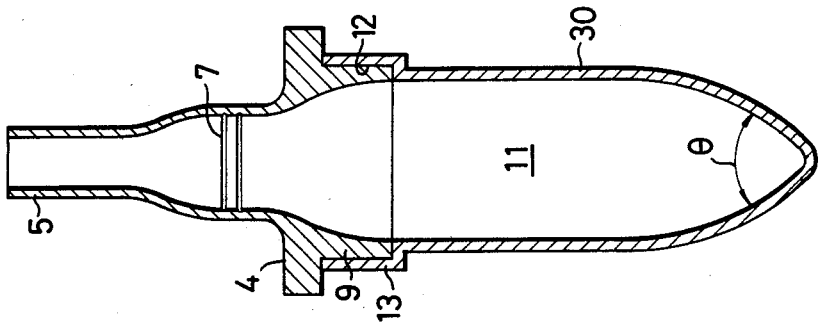

BLOOD PUMP APPLICABLE TO AN ARTIFICAL HEART

BACKGROUND OF THE INVENTION

This invention relates to a blood pump applicable to an artificial heart.

Recently, the development of an artificial heart has been made aiming at the cardiac assistance which is expected to function temporarily in place of the natural heart of a patient at the open-heart surgery. Requirements for the artificial heart call for as follows:

(1) the shape of the artificial heart should be essentially compatible with the body;

(2) the blood stream should have the least stagnant flow and the sufficient attention should be paid to the thromboregistancy.

(3) the flow-resistance should be small to maintain the sufficient blood flow by the normal venous pressure;

(4) the volume of the ventricle of the artificial heart should be pertinent to the patient's body;

(5) the artificial heart should be easily attachable to and detachable from the patient's body;

(6) the fatigue of the constituent materials of the artificial heart should be small and the sufficient durability should be guaranteed;

(7) the design of the artificial heart should be made considering the least hemolysis; and (8) the excessive negative pressure should be avoided at the ventricular distole period.

Among these requirements, (2) and (6) are the most important. The antithrombus property is influenced by hydrogynamic factors such as the design of the blood pump and roughness of the blood-contact-surface, the physical, chemical and electrical properties of the constituent materials of the artificial heart, the environmental manufacturing conditions, and so on. Especially, the design of the pump is important. Even a little modification of the shape critically influences on the blood-flow pattern in the pump. It may cause troubles in the actual long operation. The thrombosis is considered to be formed mainly due to the blood-stream conditions in the pump, particularly to the stagnation in the blood-stream. The thrombosis is complicatedly influenced by the velocity of the blood-stream, the main residence time of the blood in the pump, the shear rate of the blood at the contact-surface of the pump, etc.

For the practical use of the artificial heart, it is indispensable that the blood flux out of the pump and the pressure wave form thereof should be enough to maintain the circulation of the blood so that whole body of the patient. In other words, to function as the artificial heart, the blood pressure curves caused by the blood pump must resemble to those of the natural heart as closely as possible. Ideally, the former should be the same as the latter. When the difference of the blood pressure curve between the pump and the natural heart becomes larger than the critical level, patient's body is no longer adapted to the circumstances. In this case the patient's condition becomes bad. The most important thing to keep in mind is that the patient's conditions, who is supposed to use the artificial heart, are usually very bad. Therefore, the patient reacts so sensitively to a small difference from the natural heart, which may often become fatal.

BRIEF SUMMARY OF THE INVENTION

Accordingly, it is an object of the present invention to provide a blood pump in which the stroke pattern of the blood beaten out of the pump is scarcely fluctuated but uniform through the term for using the blood pump as an artificial heart, for example, for 3-6 months.

It is another object of the present invention to provide a blood pump which has the good antithrombus property and performance.

It is a further object of the present invention to provide a blood pump in which the design of the pump is essentially compatible with the living body, and that the pump is easily attachable to and detachable from the patient.

It is a still further object of the present invention to provide methods of manufacturing blood pumps having the good antithrombus property and performance.

In accordance with an aspect of the present invention, a blood pump comprises a housing provided with a port for introducing and discharging fluid, a cover portion for closing the housing tightly, a sac portion defining a blood chamber with the relatively flat or oval shape arranged in the housing, an inlet and outlet conduit portions for the blood, which are integrally formed on the cover portion communicating with the blood chamber and each provided with a check valve. The blood chamber is characterized in that when the blood chamber is compressed, the initial contact point from the opposite inner surfaces of the sac is regulated to locate in the area defined by a circle, the center of which is on the central axis of the wider side of the sac and in the height range between 0.2L and 0.45L from the bottom of the sac and the radius of which is 0.15D, where L is the whole height of the sac, D is the maximum width of the sac and the wider side is defined by the side projected to the vertical plane including the maximum width D of the sac.

In accordance with another aspect of the present invention, a blood pump comprises a housing provided with a port for introducing and discharging fluid, a cover portion for closing the housing tightly, a sac portion defining a blood chamber with the relatively flat or oval shape arranged in the housing, an inlet and outlet conduit portions for the blood, which are integrally formed on the cover portion communicating with the blood chamber and each provided with check valve. The blood chamber and inlet and outlet conduits are characterized in that the whole blood-contact inner surface thereof is seamless.

In accordance with a further aspect of the present invention, a method of manufacturing a blood pump comprises steps of:

(a) preparation of a cover including a pair of conduit portions, which is made from the plastisol of polyvinyl chloride;

(b) attaching the cover to a mold for a sac portion in the fluid-tight manner;

(c) pouring the plastisol of polyvinyl chloride into the mold through one of the conduit portions of the cover so that the poured plastisol is enough to contact with the cover;

(d) heating the mold so that the part of the plastisol contacting with the mold is gelled;

(e) removing the ungelled plastisol from the mold;

(f) heating the mold so as to completely cure the gelled plastisol and connect it to the cover seamlessly; and (g) removing the mold from the obtained sac portion.

In accordance with a still further aspect of the present invention, in a method of manufacturing a blood pump, a dipping process is repeated by the predetermined times, said dipping process comprising steps of dipping a mold for a sac portion and a pair of conduit portions into the solution of polyurethane and then air-dried so that a polyurethane film is formed on the outer surface of the mold.

Various other objects, advantages and features of the present invention will become readily apparent from the ensuing detailed description, and the novel features will be particularly pointed out in the appended claims.

BRIEF DESCRIPTION OF THE DRAWINGS

FIGS. 4A to 4C are vertical sections of the artificial heart showing the manner of the contraction of the blood chamber;

FIG. 8 is a vertical section of an artificial heart according to the third embodiment of the invention;

FIG. 9 is a vertical section similar to FIG. 8 showing a contraction state of the blood chamber;

FIG. 10 is a partially sectional view of a sac according to the fourth embodiment of the invention;

DESCRIPTION OF THE PREFERRED EMBODIMENTS

Figure 1:
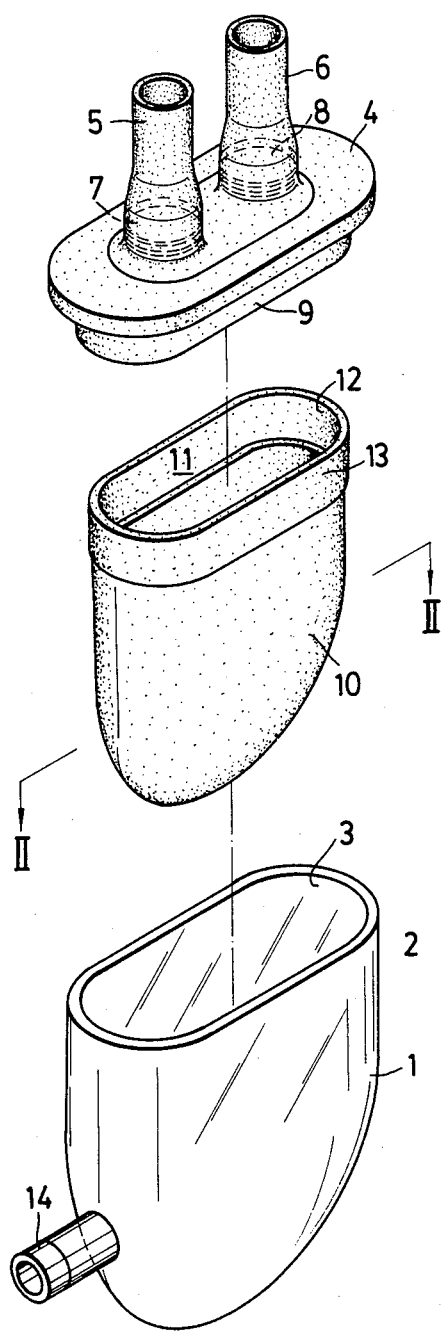
FIG. 1 is an exploded view of an artificial heart according to the first embodiment of the invention.
Figure 2:
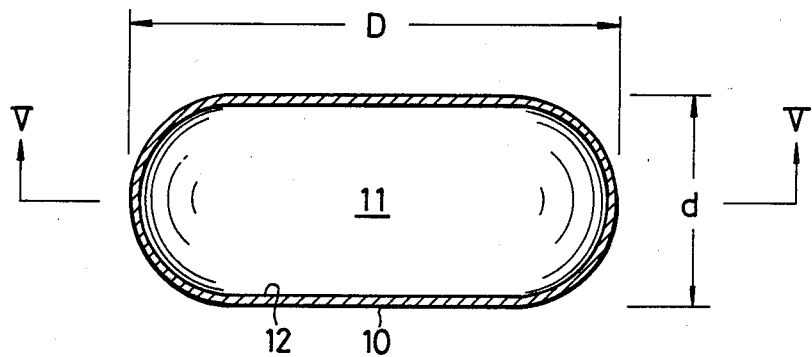
FIG. 2 is a cross-sectional view taken along the line II—II of FIG. 1.
Figure 3:
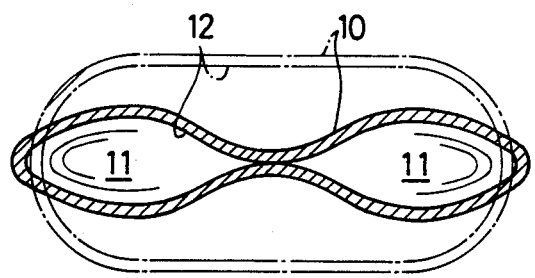
FIG. 3 is a cross-sectional view similar to FIG. 2 showing a contraction state of the blood chamber.

Referring to the first embodiment of the invention shown in FIGS. 1 to 5, an artificial heart includes an outer housing 1 made of a synthetic resin. The cross section of the housing 1 is flat or oval. At the opening 3 of the housing 1, a flange may be formed, if desired. A cover 4 made of a synthetic resin is attached fluid-tightly to the openning. The cover 4 is provided with an inlet conduit 5 and an outlet conduit 6 for the blood, which are integrally formed with the cover 4 and arranged nearly paralell with each other. In the conduits 5 and 6, check valves 7 and 8 are provided. On the inner surface of the cover 4, an annular projection 9 is integrally formed, to which a sac 10, which defines a blood chamber 11 of the pump is attached. In this embodiment, the annular projection 9 is fluid-tightly connected with the outer opening 12 of the sac 10. The fluid-tight connection is usually made by with the adhesion, ultrasonic welding or the like. Thus, the blood chamber 11 is integrated with conduits 5 and 6. The sac 10 may be made of an elastomer such as polyvinyl chloride resin with plasticizer or polyurethane and has the flat or oval cross-section as shown in FIG. 2. The cover 4 is also bonded to the housing 1 with the adhesion, ultrasonic welding or the like. Alternatively, the cover 4 can be fixed to the housing 1 with screws. The cover 4 and sac 10 can be united seamlessly with each other. Then the cover 4 is attached to the housing 1. The housing 1 has a port 14 at lower portion through which air is introduced and discharged. In this case, the pump is driven by air pressure but it may be done with any kind of fluid, for example, water, oil or carbon dioxide gas.

Next, the operation of the artificial heart according to this embodiment will be described.

First, compressed air is introduced into the housing 1 through the port 14 so that the blood chamber 11 is contracted by the pressure as shown in FIGS. 4A to 4C. Thereby, the blood in the chamber 11 is squeezed out through the check valve 8 of the outlet conduit 6 while the check valve 7 of the inlet conduit 5 is closed. Next, the pressure in the housing 1 is reduced. The sac 10 is expanded to its original state or more. As the volume of the blood chamber 11 is increased, blood is introduced into the chamber 11 through the opened check valve 7 of the inlet conduit 5 while the check valve 8 of the outlet conduit 6 is closed. The above operations are repeated alternately, thereby the blood is intermittently beaten out.

In order that the blood pump satisfactorily functions as the artificial heart for asisting the natural heart, the operation pattern according to the expansion and contraction of the blood chamber 11 at the beat rate of 60-120 min. must be always uniform without any happening of an unusual pattern through the long operation: at least one month. That is, during the countless heartbeats, the mode of action of the sac 10 discharging the blood must be kept in the same pattern. For this purpose, the most important point is that the initial picture of the deformation of the sac 10 must be kept uniform. According to inventor's finding, the location of the initial contact point between the opposite inner surface of the sac 10 is very important. The picture of deformation of the sac 10 by the change of the air pressure is shown in FIGS. 4B and 4C.

In this embodiment, the cross-section of the sac 10 must be flat or oval shape as shown in FIG. 2. In this connection, the more detailed analysis will be given with reference to FIG. 5. The figure shows a vertical section of the sac 10 which is taken along the longest axis of the cross-section thereof. Hereinafter, the side of the sac 10 projected to the plane of FIG. 5 is called "the wider side".

Figure 5:
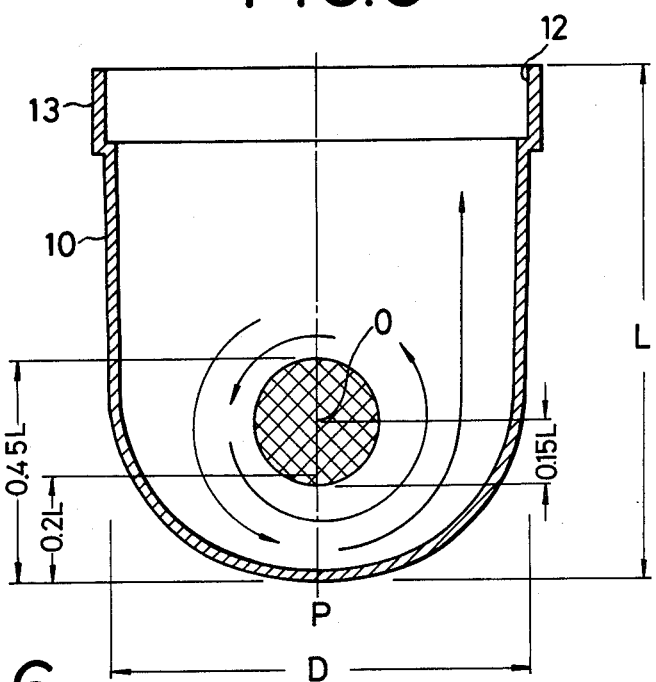
FIG. 5 is another vertical section taken along the line V—V of FIG. 2.

As already mentioned, initial contact point from both wider side of the sac 10 must be located in an area indicated by shadow in FIG. 5. This area is defined as follows. Here, the whole height of the sac 10 is L and the width of the wider side, that is, the maximum width of the sac 10 is D. The area is defined by a circle. The center O of the circle is located on the vertical central axis P of the wider side. Here, "vertical" means the direction along the conduits 5 and 6. The center point O must be within the height range between 0.2L and 0.45L, preferably 0.2L and 0.4L from the bottom of the sac 10. The radius of the circle is 0.15D, preferably 0.1D, more preferably 0.08D. The inventor formed that when the initial contact point of the inner surface of the sac 10 is strictly regulated to locate in the above-mentioned area, the mode of the deformation-picture of the sac 10 can be kept uniform in the long term. In this case, it is notable that the blood streams in the chamber are quite uniform and regular, the circular streams are shown by the arrows in FIG. 5. This ideal circular blood stream is produced when the bottom of the blood chamber is designed so that vertical section thereof is characterized with semi-circular shape as shown in FIG. 5. On the contrary, when the initial contact point dislocates out of the circle, the fluctuation arises in the pattern of the action of the sac 10. The unusual mode of action of the sac causes the unusual discharging pattern of the blood output from the pump, which influences on the patient condition. As a result, fatal bad influence often occurs on the patient to whom the artificial heart is applied.

According to the present inventor's study, a flat shape as shown in FIG. 2 is very effective to keep the initial contact point in the above-mentioned specified area. The flatness (F) at the cross-section, which is defined by the rate of the maximum width D of the sac 10 to the maximum width d perpendicular to the former, at the unloaded condition, should be within the range of 2.0 to 4.0, preferably 2.1 to 3.5, more preferably 2.2 to 3.0. When the flatness F is within the above range, uniform action of the deformation of the sac 10 can be obtained.

When the flatness F is below 2.0, various distorted deformation of the sac 10 often arises and from the practical point of view, such artificial heart can not be clinically applied. For example, when the blood chamber is cylindrical (the flatness F is 1), it was experimentally clear that the mode of the compression of the sac is not uniform. When the cylindrical sac is compressed by the air pressure, the portion of the sac starting the deformation is not defined in every beat and the manner of the volume-change of the blood chamber is variously fluctuated. Further, the minimum volume of the blood chamber is varied in every beat. Therefore, such artificial heart is impossible to keep uniform blood-output from the pump and the blood pressure curve thereof. On the other hand, when the flatness F is above 4.0, the expansion behavior of the sac 10 by the reduced pressure becomes unstable.

In this embodiment, the initial contact point is regulated to locate in the predetermined area by the above-mentioned manner. Thus, the opposite inner surfaces of the sac 10 contact with each other firstly at the regulated initial contact point from which the contact surface area between the inner surfaces spreads out. By this manner, the uniform circular blood stream along the side wall of the pump is always reproduced in the blood chamber 11 so that the blood may beat out through the valve 8 in the same behavior at each heart beat. Uniform circular blood stream in each beat thus produced can prevent the blood from the thrombus formation in the chamber 11.

In this embodiment, the blood contact surfaces, for example, the inner surface of the sac 10, and conduits 5 and 6 may be made of elastomers like polyvinyl chloride containing plasticizer or polyurethane. Instances of the plasticizer may be dioctyl phthalate (DOP), dibutyl phthalate (DBP), butyl benzyl phthalate (BBP), dioctyl adipate (DOP), butyl phthalyl butylglycolate (BPBG), methyl acetyl ricinolate (MAR), acetyl tributyl citrate (ATBC) and the other known plasticizers for polyvinyl chloride. Amount of plasticizer, the ranges from 40 to 100% by weight, more preferably 50-80% by weight based on the polyvinyl chloride. In addition, the suitable stabilizer, for example, nontoxic calcium-zinc organic compound may be added to the polyvinyl chloride. The degree of polymerization of polyvinyl chloride is preferably 500 to 2000.

Polyurethane to be used in this embodiment is devided into two categories, one being polyether-polyurethan (polyurethane of polyether origin), another being polyester-polyurethane (polyurethane of polyester origin), both of which can be used. However the polyether-polyurethane is preferably used because of the better elastic property and better fatigue resistancy.

Polyurethane can be obtained by the reaction between diisocyanate and polyol. Diisocyanate used in this embodiment are tolylene diisocyanate (TDI), 4,4'-diphenylmethane diisocyanate (MDI), 1,6-hexamethylene diisocyanate (HDI), 1,5-naphthalene diisocyanate (NDI), 3,3'-dimethoxy-4,4'-biphenyl diisocyanate (TODI), phenylene diisocyanate (PDI), 4,4'-biphenyl diisocyanate, etc.

The polyol used in polyester-polyurethane are adipate groups with hydroxyl groups at the both ends, for example, poly-(ethylene adipate), poly-(propylene adipate), poly-(1,4-butylene adipate), poly-(1,5-pentylene adipate), poly-(1,3-butylene adipate), poly-(ethylene succinate), poly-(2,3-butylene succinate), etc. The polyester-polyurethane forms harder elastomer having the high modulus and good tear strength. Therefore, it is suitable for the cover 4 and conduits 5 and 6.

The sac 10 requires high elasticity, good elastic recovery and fatigue resistancy. Therefore, polyether-polyurethane is preferable for the sac.

Examples of polyether used for the polyurethane are tetramethylene glycol, polyethylene glycol, polypropylene glycol, pentamethylene glycol, diglyme, etc.

Polyether-polyurethane can be made as follows. The above-mentioned glycol group is reacted with diisocyanate to obtain the prepolymer having hydroxyl groups at the both ends, then the prepolymer is reacted with compounds having diisocyanate groups at the both ends. Alternatively, the above-mentioned glycol group is reacted with diisocyanate to obtain the prepolymer having diisocyanate groups at the both ends, then the prepolymer is subjected to react with diamine or diol as chain extender. Further, so-called segmented-polyurethane which is composed of soft segments and hard segments may be used. Soft segments (which is defined by the lower secondary transition temperature) are usually polyether chain with hydroxyl groups at the both ends, and hard segments are the part of molecule with benzene ring and/or symmetrical structure in the chain.

Polyurethane may be underwent cross-linking in order to increase the mechanical strength thereof. Instances of the cross-linking agent are N,N,N',N'-tetrakis(2-hydroxy propylethylene diamine), 4,4′-methylene-bis(2-chloroaniline), 4,4′-diaminodiphenylmethane, 3,3′-dichloro-4,4′-diaminodiphenylmethane benzidine, 3,3′-dimethyl benzidine, 3,3′-dimethoxy benzidine, 3,3′-dichlorobenzidine, p-phenylene diamine, etc. The cross-linking can be effected by the heat treatment after addition of the above-mentioned cross-linking agents. The amount of the cross-linking agents is preferably 0.01–5 wt. %, more preferably 0.1–3 wt. % based on the polyurethane. Besides, the temperature of the heat treatment is preferably 60° to 150° C., more preferably 80° to 120° C., still more preferably 80° to 110° C.

When the sac 10 is made of soft polyvinyl chloride which means polyurethane with plasticizer, the thickness of the sac is preferably 0.5 to 2.0 mm, more preferably 0.6 to 1.5 mm, still more preferably 0.8 to 1.2 mm in consideration of the restitution and fatigue-resistance, properties. When the sac 10 is made of polyurethane, the thickness thereof is preferably 0.3 to 1.5 mm, more preferably 0.4 to 1.2 mm, still more preferably 0.8 to 1.0 mm. When the thickness is greater than the above-mentioned range, it is difficult to obtain the preferred movement of the sac 10 for beating out the blood, because thicker wall causes the delayed timing of the movement of the sac, thus, fails to react smoothly with the changes of the pressure in the housing 1. Besides, the required time for the deformation of the sac 10 elongates. On the other hand, when the thickness of the sac 10 is smaller than the above-mentioned range, the control of the action of the sac 10 becomes difficult, because the sac 10 becomes too sensitive to the change of the pressure.

For the valves 7 and 8, the commercial valves may be used. Such valves are the ball type, disk type, leaflet type, etc. Particularly, the Bjork-Shilley valve which is a disk valve of the hinge type is preferably used.

In the artificial heart according to this embodiment, the surface which contacts with the blood may be coated with the material showing the good antithrombus property to improve the blood compatibility. For example, the surface treatment are made with an anticoagulant material for blood such as dimethyl siloxane, and/or polyurethane, the block-copolymer of polyurethane and polydimethyl siloxane, in which polyetherpolyurethane is preferable and a blend of polyurethane and polydimethyl siloxane, if desired, cross-linked polydimethyl siloxane, or interpenetrating copolymer of polyurethane and polydimethyl siloxane, and so on. It is found effective that at least the sac 10 is made of polyvinyl chloride substrate including the plasticizer and the unticoagulant material layer of 1–300μ thickness, which contacts with the blood, is formed on the surface of the substrate.

FIGS. 6 to 12 show various modified embodiments of the invention. In these embodiments, the construction of each artificial heart but the parts specified hereinafter is the same as that of the above-mentioned embodiment.

Figure 6:
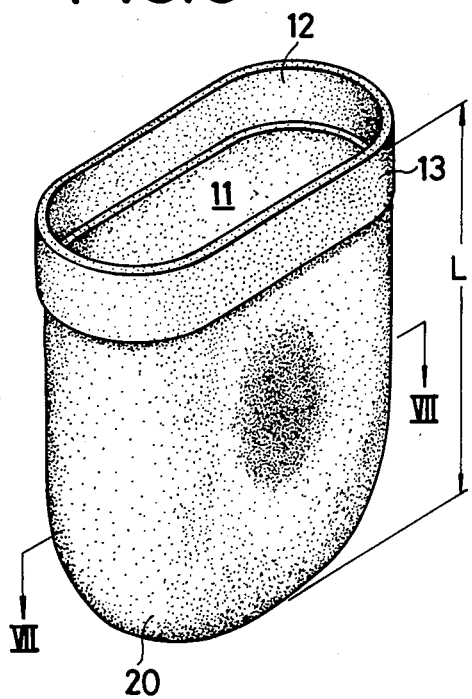
FIG. 6 is a perspective view of an envelope according to the second embodiment of the invention.
Figure 7:
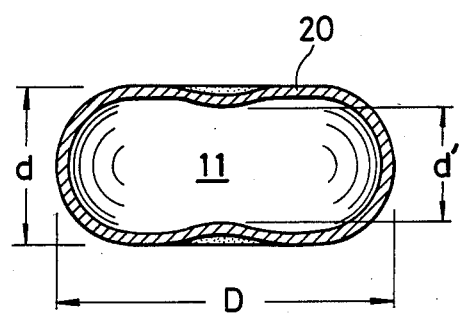
FIG. 7 is a cross-sectional view taken along the line VII—VII of FIG. 6.

FIGS. 6 and 7 show the second embodiment, of the invention. In this embodiment, each of the opposite wider sides of the flat shaped sac 20 are gradually curved inside at the unloaded condition. In this case, the ridge of the curved portion coincides with the vertically central axis of the wider side. This construction effects to regulate the initial contact point above defined on the vertically central axis of the wider side and within the regulated range proposed in this invention. In this embodiment, each of the wider sides may be curved also in the vertical direction in FIG. 6 so that the peak of the curved portion locates in the area defined by the invention. Also, only the neighbourhood of the initial contact point to be regulated may be dented from both wider sides so that the peak thereof may firstly contact with each other.

FIGS. 8 and 9 show the third embodiment of the invention. In this embodiment, the bottom of the sac 30 of the relatively flat shape has the nearly V-shaped vertical section taken along the plane perpendicular to the wider side. This construction, effects to regulate the initial contact point from both opposite wider sides in the area defined by the invention. Preferably the opposite wider sides can closely contact with each other around the bottom portion. Accordingly, the better compression pattern of the blood chamber 11 can be obtained, namely the side portions of each wider wall are smoothly compressed. The compression begins around the bottom portion of the chamber 11, and then the contact-area is gradually and uniformly out-spreads to the upper part with concomitant compression of the sides. The V-shaped vertical section (we call "ridge bottom" hereafter) is formed at around the bottom of the chamber. The ridge bottom is preferably formed at the parts lower than those having 0.9D. The dihedral angle $\theta$ defined by the opposite wider sides is 30° to 120°, preferably 40° to 100° more preferably 50° to 70°, still more preferably around 60°. When the dihedral angle is below 30°, the bottom portion of the sac 30 becomes too flat. On the other hand, when the dihedral angle is above 120°, the bottom portion of the sac 30 is hard to be compressed. In this embodiment, a thinner bottom ridge of the sac 30 effects to, facilitate the deformation of the sac 30. Thus the thinner bottom ridge is preferable.

FIG. 10 shows the fourth embodiment of the invention. In each wider side of a sac 40 of the relatively flat shape according to this embodiment, a thinner portion 41 is formed, the thickness of which is smaller than the mean thickness of the sac 40. The thinner portion 41 is centered by the initial contact point to be regulated in accordance with the invention and has a predetermined area. Because the thinner portion 41 is more deformable by the external pressure than the other portion, the opposite wider sides of the sac 40 can contact with each other initially at the thinner portion 41. In this case, the thinner portion 41 may be made by reducing the wall thickness from the outer and/or inner surfaces of the wall of the sac 40. The thickness of the thinner portion 41 is 3 to 50% less than the mean thickness of the sac 40 and preferably 3 to 50% less, more preferably 5 to 30% less. The area of the thinner portion 41 is preferably defined by a circle, the center of which is the predetermined initial contact point and the diameter of which is nearly $\frac{2}{3}D-\frac{1}{2}D$ (D is the largest width of the envelope 40). The thinner predetermined portion is not always shaped circular, but it may be rectangular, square or the other polygons with round corners. Besides, the thickness of the thinner portion 41 may be gradually changed so that the thickness at the predetermined initial contact point may be the smallest.

Figure 11:
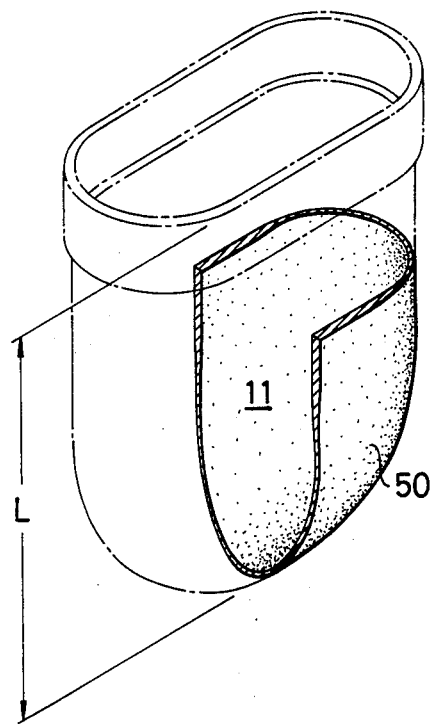
FIG. 11 is a partially sectional view of a sac according to the fifth embodiment of the invention.

FIG. 11 shows the fifth embodiment of the invention. In this embodiment, the thickness of the bottom portion and/or the both side portions of the wider sides of the sac 50 is thinner than that of the other portions. Therefore, by the thinner bottom portion, the initial contact point is more effectively regulated to locate in the area defined by the invention. Besides the deformation at the both side portions of the wider side becomes easier by the smaller thickness. This means the uniform compression can spread almost whole part of the sac which eliminates any stagnant part of the blood in the pump. This greatly effects to prevent the thrombos formation. The blood coagulation in the bottom and the both sides of the blood chamber observed so far is thus completely eliminated by this invention. The compression pattern of the blood chamber 11 are so smooth in this embodiment. The thickness of such thinner portion is 5 to 80% less, preferably 10 to 70% less, more preferably 10 to 50% less than the mean thickness of the envelope 50. The thinner bottom portion is formed up to the height of $\frac{1}{2}L$ (L is the whole height of the sac 50). The thinner bottom portion can be limited in the ridge of the bottom. Concerning the thinner side portions, the thickness can be reduced either continuously or partially. Each thinner side portion is preferably formed along the vertically central axis of the narrow side of the sac 50 (which is the side, perpendicular to the wider side). In this case, the thinner portion may be formed at least on the central vertical axis of the narrow side.

Figure 12:
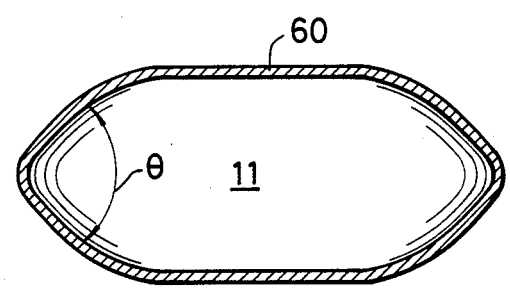
FIG. 12 is a cross-sectional view of a sac according to the sixth embodiment of the invention.

FIG. 12 shows the sixth embodiment of the invention. In this embodiment, both narrow side of a sac 60 has the nearly V-shaped cross-section. This V-shaped side-wall may be formed around the bottom portion, and may be up to the $\frac{1}{3}$ or half height of the sac. The V-shaped side wall may also be formed on the whole height of the narrow side wall of the sac. By this construction, the both side portions of each wider side are smoothly compressed, thus blood-stagnancy at the side of the blood chamber can be effectively eliminated. By using this construction of the chamber the compressed portion are gradually and uniformly spread out from the bottom to the upper part ideally. Thus, the uniform compression pattern of the blood chamber 11 can be always obtained. The dihedral angle $\theta$ defined by the opposite wider sides is 30° to 120°, preferably 45° to 100°, more preferably around 60°. When the dihedral angle is below 30°, the sac 60 becomes too flat. On the other hand, when the dihedral angle is above 120°, the both side portions of the sac 60 becomes difficult to be compressed. In this embodiment, it is more effective that the both side portions of the sac 60, namely the neighbourhood of the central axis of each narrow side is relatively thinned so as to facilitate the deformation.

In the above-mentioned all embodiments, it is effective that the whole inner blood-contact surface is made seamless. The reason is that, if there is uneven portions on the inner surface of the artificial heart, for example, the seam between the sac 10 and conduits 5 and 6, the bloodstream is disturbed at the uneven portion. As a result, the thrombus is quickly formed therefrom. This kind of trouble can be eliminated by the seamless inner surface of the artificial heart.

Next, the manufacturing processes of the artificial heart having the seamless inner surface will be described.

Figure 13A:
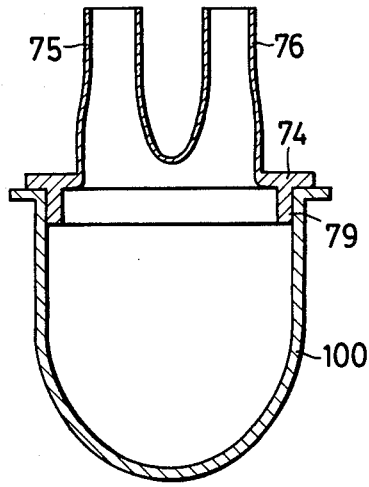
FIGS. 13A to 13F are vertical sections showing steps of a manufacturing process of a blood chamber.
Figure 13B:
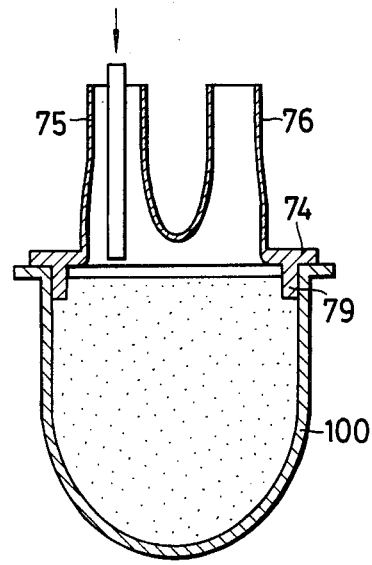

Referring to FIGS. 13A–13F, a cover 74 with a pair of conduit portions 75 and 76 is manufactured from the plastisol of polyvinyl chloride by the dipping process as described hereinafter. At this time, an annular projection for receiving the check valve may be formed in each of the conduit portions 75 and 76. Alternatively, a pair of conduit elements each including the valve may be connected to the cover. The cover 74 is provided with an annular projection 79 and the latter is inserted fluid-tightly into a metal mold 100 as shown in FIG. 13A. Then, the plastisol of polyvinyl chloride (for example, Type-131A, Nippon Zeon Co. Ltd.) is poured into the mold 100 to the predetermined level as shown in FIG. 13B. Then, the mold 100 is dipped into the heating bath. The heating temperature is in the range of 70° to 150° C., preferably 80° to 110° C. When the polymer used in the plastisol is not a homopolymer of vinyl chloride but the copolymer having the lower softening temperature such as vinyl chloride-vinyl acetate copolymer and vinyl chloride-vinyl ether copolymer, the heating temperature may be relatively low. The treatment time in the heating bath is preferably a few minutes to 30 min. When the heating is insufficient or the treatment time is too short, the thickness of the gelled layer obtained is too small. On the contrary, when the temperature is too high or the treatment time is too long, the thickness of gelled layer becomes too large.

Figure 13C:
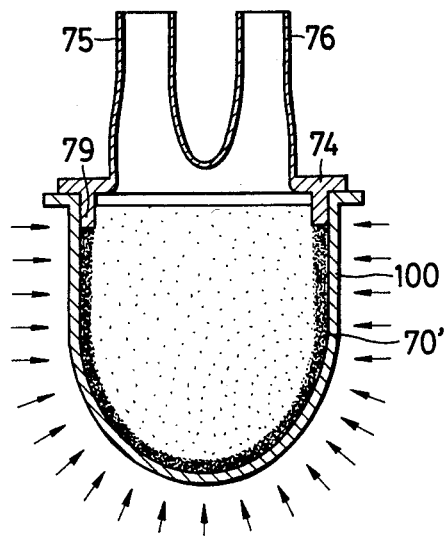
Figure 13D:
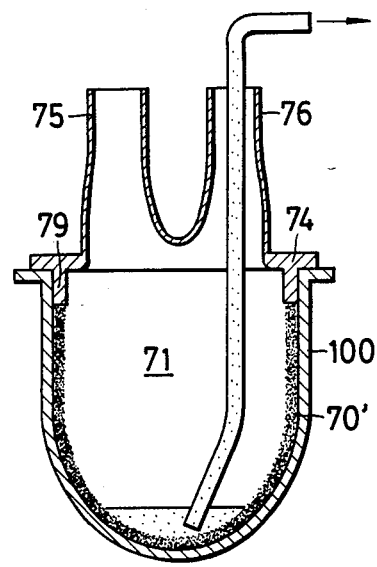
Figure 13E:
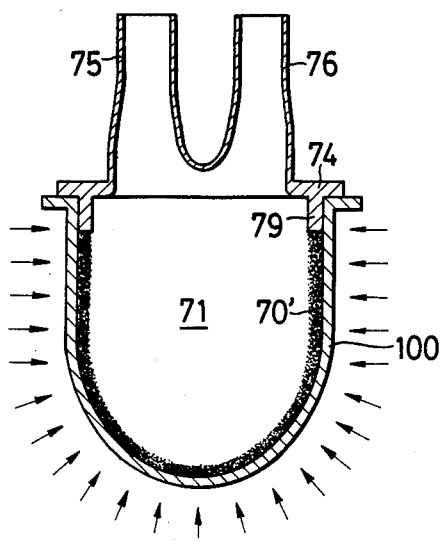
Figure 13F:
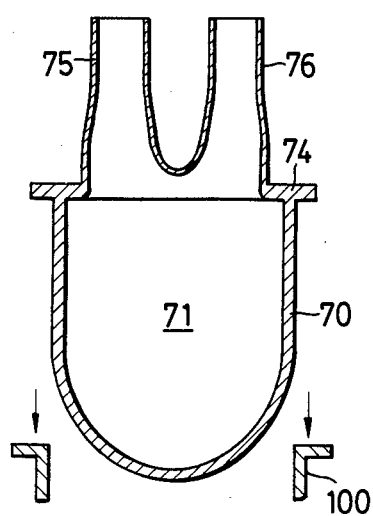

In this treatment, the part of the plastisol contacting with the mold 100 is gelled by the heat and adheres to the inner surface of the mold 100 to form a gelled layer 70' of the predetermined thickness as shown in FIG. 13C. At this time, there is the plastisol inside of the annular projection 79 which is formed integrally with cover 74, this plastisol is not gelled because of the heat insulation effect of the annular projection 79. Therefore, this part of the plastisol flows down by the gravity during the procedure of discharging the paste as shown in FIG. 13D. Thereby the surface of the gelled layer 70' is integrated so that the even and seamless inner surface of the blood chamber 71 is obtained. Subsequent the heat curing results in the even and seamless inner surface in the result as shown in FIGS. 13E and 13F. The heating temperature in this step is preferably 160° to 240° C., more preferably 190° to 210° C. When the heating temperature is below 160° C., the curing is insufficient. When the temperature is above 240° C., polymer may decompose or discolour. Then, after being cooled, the mold 100 is removed as shown in FIG. 13F. By this procedure, seamless blood-pump can be produced.

The above-mentioned process can be applied to the aquatic plastisol and, of course, may be applied to the organosol in which the organic solvent is used as a dispersion medium.

Figure 14A:
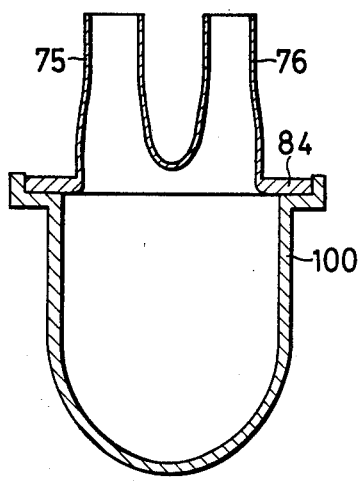
FIGS. 14A and 14B are vertical sections showing steps of another manufacturing process of a blood chamber.
Figure 14B:
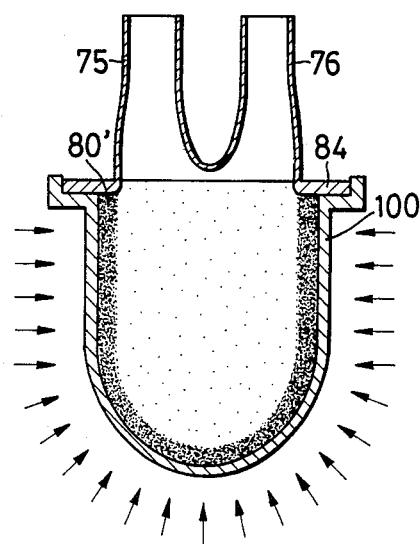

Next, referring to FIGS. 14A and 14B, another process will be described. In this process, a cover 84 is made of epoxy resin and provided with no annular projection. The cover 84 is attached fluid-fight to a metal mold 110 for the slush molding in the similar manner to the above-mentioned process as shown in FIG. 14A. Then, the plastisol of polyvinyl chloride is poured into the mold 110 to the level which is a little higher than the lower end surface of the cover 84 as shown in FIG. 14B. The subsequent operations may be the same as shown in the above-mentioned process shown in FIG. 13. In this case, the part of the plastisol inside of the cover 84 is not gelled because of the heat insulation of the cover 84 and so flows down along the surface of the gelled layer 80' in the step of discharging the plastisol so that the inner surface may be smooth integrated seamless.

By the above-mentioned two processes, the blood pump mainly made from soft polyvinyl chloride for the use of the artificial heart can be formed in one body, which has the seamless inner surface.

In this embodiment, when the cover is formed from the plastisol of polyvinyl chloride, relatively low content of the plasticizer may be preferable. Example of suitable plastisol component are the one comprising 100 parts of polyvinyl chloride, 40 to 60 parts of dioctyl phthalate as the plasticizer and 3 parts of a calcium-zinc organic composite. On the other hand, the blood chamber must have more flexible nature and better elasticity because the chamber must deform repeatedly accompanied the change of the external air pressure in every beat. The plastisol suitable for the sac preferably comprises 100 parts of polyvinyl chloride and 70 to 90 parts of dioctyl phthalate.

Next, it will be described that a process to manufacture the blood pump of polyurethane having the seamless inner surface.

Figure 15A:
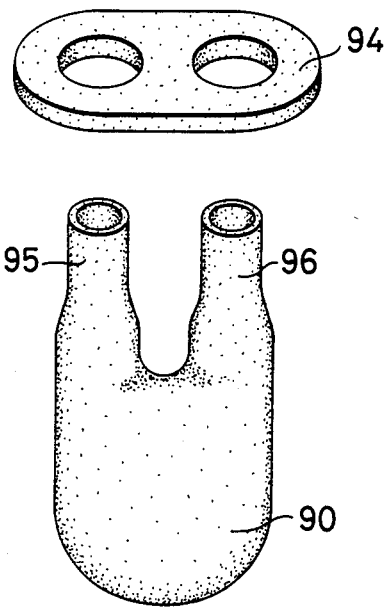
FIG. 15A is an exploded view of a blood vessel and a brim member.
Figure 15B:
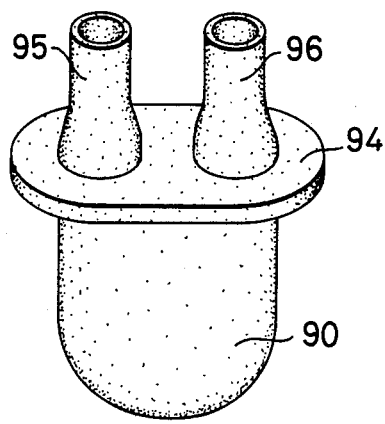
FIG. 15B is perspective view of the assembled blood vessel.

First, a mold is made from paraffin or wax into the predetermined shape including the sac and a pair of conduits. The mold is dipped into the solution in which polyether-polyurethane is dissolved in dimethylformamide at the concentration of 6–20%, preferably 8 to 15%, and then air-dried (This operation is called "dipping process" hereafter). The solution may be made of the one of the group consisting of dimethyl acetoamide, dimethyl-formamide, tetrahydrofuran, and dioxane. This operation is repeated, for example, about 30 times. In the operation, the polyurethane film formed on the mold may be subjected to extraction with water in a proper time for the complete removal of the solvent. In this manner, the polyurethane film of suitable thickness on the mold can be obtained seamlessly. After the predetermined film thickness of the sac is obtained, the inlet and outlet conduits portions may be further subjected to the dipping processes predetermined times so that the thickness of the conduits can be larger than that of the sac. For the dipping of the conduit portions, the solution of polyester-polyurethane, which has the relatively large stiffness, may be used so as to obtain the harder conduits. Then, the mold on which the polyurethane film is formed is heated to the temperature higher than the melting point of paraffin or wax. The melted liquid paraffin or wax is removed from the molded polyurethane member. Polyurethane blood-chamber with two conduits thus formed is washed with the suitable solvent. As shown in FIG. 15, a vessel thus formed comprises a pair of thicker inlet and outlet conduit 95 and 96 portions and a thinner sac portion 90 and has seamless inner surface.

Then a brim member 94 is attached to the conduit portions by insertion through holes of the brim member and connected each other fluid tightly for example, by adhesion as shown in FIG. 15. Alternatively, the brim member may be connected to the vessel during the dipping process in such a way that the brim member is fixed at the predetermined position. Then, the sac portion of the vessel is placed into a housing and the brim portion is bonded to the housing. Thus, a blood pump of polyurethane which has the seamless inner surface can be obtained.

Besides, in the above-mentioned process, a separable metal mold having the vertical separation line may be used in place of the mold of paraffin or wax.

Next, experimental results will be described.

Figure 16:
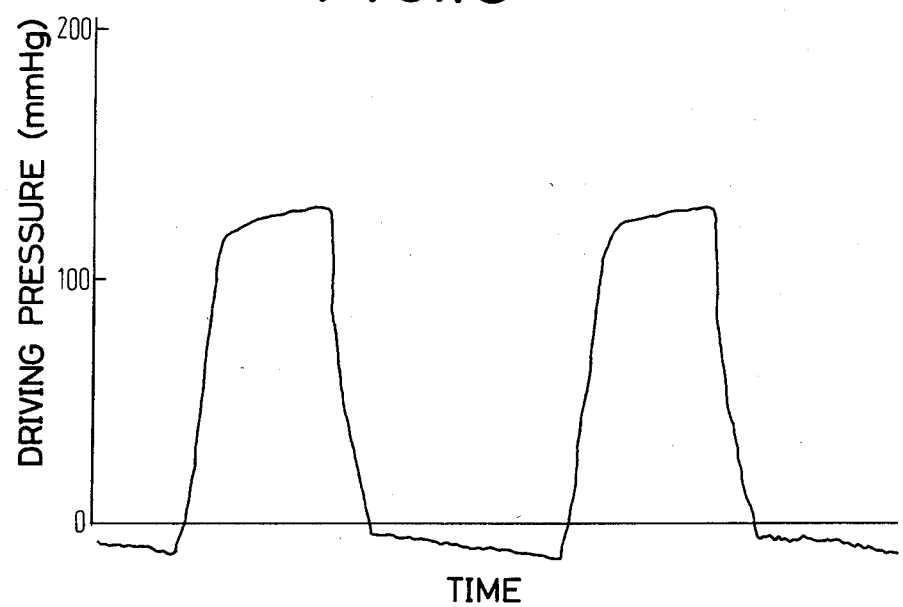
FIG. 16 is a wave form chart of the driving pressure in an artificial heart according to an embodiment of the invention.
Figure 17:
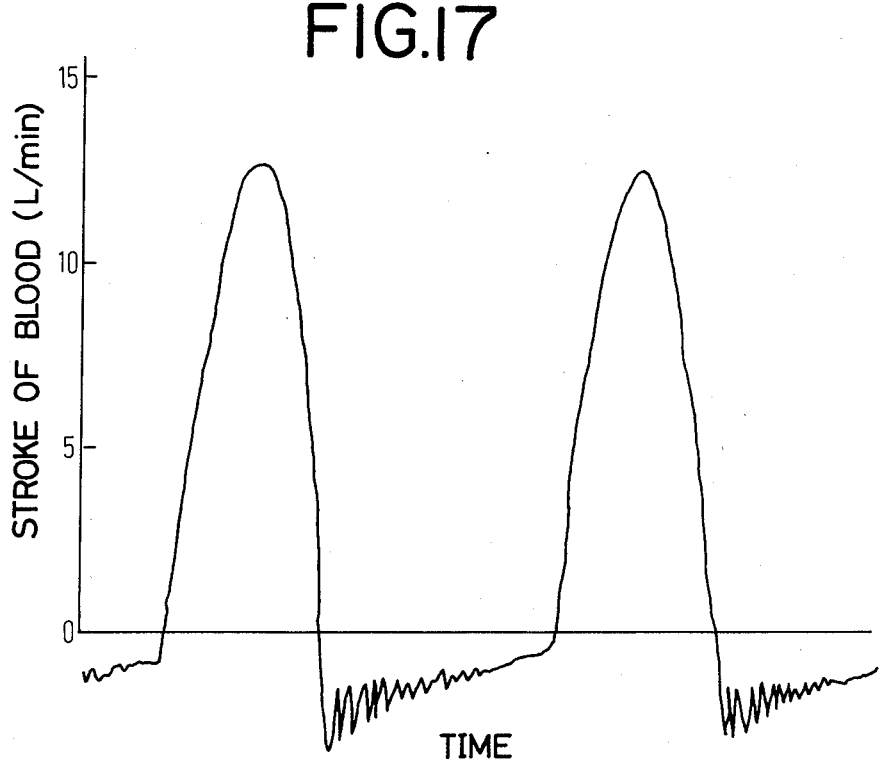
FIG. 17 is a wave form chart of the stroke of the blood in the artificial heart of FIG. 16.

In the experiment, a blood pump according to the second embodiment of the invention as shown in FIGS. 6 and 7 was employed. The flatness F was 2.3, and the whole height L was 63 mm and the maximum width D was 63 mm. In the cross section of the sac 20 shown in FIG. 7, the maximum width d perpendicular to the maximum width D was 26 mm and the minimum distance d' between the opposite dented portions of the wider sides was 24 mm. The sac 20 of polyurethane was arranged in a housing made from polycarbonate and Bjork-Shilley valves were employed as the check valves. The volume of the blood for filling up the blood chamber 11 was 75 ml. The negative pressure for driving the pump was 40 mmHg, the beat rate was 90/min. the pressure at the inlet of the pump was 200 mmHg and the pressure at the outlet was 104 mmHg. The stroke of the blood beaten out from the pump and the waves of the stroke volume were measured with an electromagnetic flowmeter (made by Nihon Kohden Kogyo Co. Ltd., 14 mm$\phi$) which was attached to the outlet of the pump. Simultaneously, the driving pressure in the housing and the wave form were measured with a piezeolectric gauge. The above-mentioned pressures at the inlet and outlet of the pump were measured with water column and mercury manometers. Examples of the wave forms of the driving pressure and stroke of the blood are shown in FIGS. 16 and 17, respectively. In the experiment of the simulative operation for a month, these wave forms were completely stable and uniform through the above-mentioned term.

Figure 18:
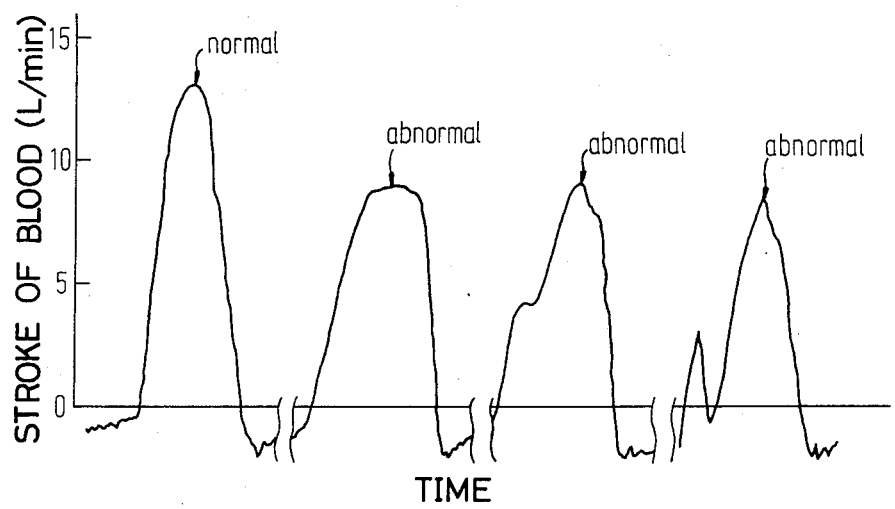
FIG. 18 is a wave form chart of the stroke of the blood in an artificial heart according to a comparison example.
Figure 19:
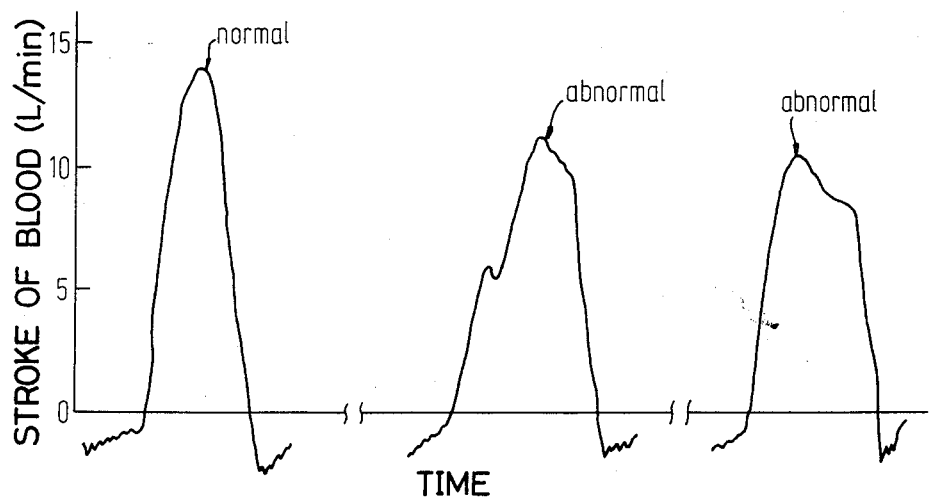
FIG. 19 is a wave form chart of the stroke of the blood in an artificial heart according to another comparison example.

For comparison, similar experiments were carried out, in which a blood pump having the same volume of the blood chamber but a cylindrical sac (comparison example A) and a blood pump having a flat sac of the flatness F=1.88 (comparison example B) were employed. The blood chamber of example B has the maximum width D of 62 mm, and the whole height L of 33 mm and the volume of the blood for filling up the blood chamber was 80 ml. For the comparison example A, the wave form of the driving pressure was the same as that shown in FIG. 16 but the wave form of the stroke of the blood was multifariously changed. Some typical instances thereof are shown in FIG. 18. In other words, when the blood chamber of cylindrical shape was used, the stroke pattern of the blood beaten out of the pump was considerably fluctuated. In the comparison example B, the stroke pattern of the blood was not so unstable like the comparison example A, because the sac has flat shape to some extent. But the blood stroke pattern was sometimes fluctuated (as shown in FIG. 18). In the mock driving test, the initial contact point between the opposite wider sides of the sac of the comparison example B sometimes dislocated out of the area defined by the invention. From this fact, it became apparent that there is a mutual relation between the initial contact point of sac and the fluctuation of the stroke pattern of the blood.

Next, the relation of the flatness F and the location of the initial contact point in view of the frequency of the fluctuation of the stroke pattern was examined by a series of the simulative experiments (the beat rate was 90/min.) for 23 days. The experimental results are given in the following table.

TABLE

| Flatness of the sac | 1/1 | 1.3/1 | 1.5/1 | 1.7/1 | 1.7/1* | 1.8/1 | 1.8/1* | 1.8/1** | 2.0/1 | 2.0/1* | 2.2/1 | 2.5/1 | 3.0/1 |
|---|---|---|---|---|---|---|---|---|---|---|---|---|---|
| Mean frequency of the abnormal patterns (/min.) | 67 | 59 | 59 | 32 | 12 | 29 | 10 | 13 | 1 | 0 | 0 | 0 | 0 |
| Distance of the initial+ contact point out of | 16 | 17 | 12 | 9 | 2 | 6 | 1 | 2 | 1 | 0 | 0 | 0 | 0 |

TABLE-continued

| Flatness of the sac | 1/1 | 1.3/1 | 1.5/1 | 1.7/1 | 1.7/1* | 1.8/1 | 1.8/1* | 1.8 /1** | 2.0/1 | 2.0/1* | 2.2/1 | 2.5/1 | 3.0/1 |
|---|---|---|---|---|---|---|---|---|---|---|---|---|---|
| the area defined by the invention (mm)⁺ | | | | | | | | | | | | | |

⁺ The mean distance in 30 times of the mock driving test.
*The sac in which the wider side was curved inside was used; (The depth of the dented portion was about 1 mm.) Wider side wall is not curved inside unless otherwise noted.
**The sac in which the neighbourhood of the contact point was thinner was used. (The thickness was 30% less.)

As apparent from the results, when the flatness of the sac is more than 2.0, the initial contact point scarcely dislocates out of the area defined in the invention. The frequency of the fluctuation of the stroke pattern is very few in comparison with that in which the flatness F is below 2.0. It is also shown that when the wider sides of the sac is curved inside or the thickness of the sac wall at the neighbourhood portion of the initial contact point is smaller, the dislocation of the initial contact point from the predermind area becomes smaller. In these cases the frequency of the fluctuation of the stroke pattern is fairly reduced in comparison with that for the blood chamber having the same flatness but having no curved or thinner sac wall.

I claim:

1. A blood pump comprising:
   (a) a housing provided with a port for introducing and discharging fluid;
   (b) a cover portion closing the housing tightly;
   (c) an inlet conduit portion formed integrally and seamlessly into said cover, said inlet conduit portion including a check valve;
   (d) an outlet conduit portion formed integrally and seamlessly into said cover, said outlet conduit portion including a check valve; and
   (e) a flexible sac portion defining a blood chamber, said sac portion being oval in cross-section, curved at the bottom, and seamlessly connected to said cover portion, having a maximum width D, a maximum height L and a thickness of that portion below the line described by $\frac{1}{2}L$, which is between 20% and 95% less than the mean thickness of the sac wherein, when the volume of the blood chamber is decreased, the initial contact point between the opposite inner surfaces of the sac is in the area defined by a circle of radius 0.15D the center of which is on the central axis of the wider side of the sac and between 0.2 and 0.45L above the bottom of the sac.

2. A blood pump according to claim 1, in which the flatness of the sac is in the range between 2.0 and 4.0, where the flatness is defined by the rate of the maximum width D of the sac to the maximum width d perpendicular to the former when they are measured at the unloaded condition.

3. A blood pump according to claim 1, in which the bottom of the blood chamber is designed so that the vertical section thereof taken along the plane including the maximum width of the sac has a semicircular shape.

4. A blood pump according to claim 1, in which at least one of the opposite wider sides of the sac is curved inside the blood chamber at the unloaded condition, the ridge of the curved portion coinciding with the vertically central axis of the wider side.

5. A blood pump according to claim 1, in which at least one of the opposite wider sides of the sac is curved in the vertical direction at the unloaded condition so that the peak of the curved portion locates in the defined area for the initial contact point.

6. A blood pump according to claim 1, in which the neighbourhood portion of the initial contact point to be regulated is formed into the dent on at least one of the opposite wider sides of the sac so that the peak of the dent portion corresponds to the initial contact point.

7. A blood pump according to claim 1, in which the bottom portion of the sac has the nearly V-shaped vertical section taken along the plane perpendicular to the wider side at the unloaded condition so that the dihedral angle is defined by the opposite wider sides.

8. A blood pump according to claim 7, in which the dihedral angle defined by the opposite wider sides of the sac is in the range between 30° and 120° at the unloaded condition.

9. A blood pump according to claim 1, in which a thinner portion specifying a predetermined area, the thickness of which is smaller than the mean thickness of the sac, is formed on at least one of the opposite wider sides of the sac, the center of the thinner portion corresponding to the initial contact point to be regulated.

10. A blood pump according to claim 9, in which the thickness of the thinner portion is in the range between 3% less and 50% less than mean thickness of the sac.

11. A blood pump according to claim 9, in which the thinner portion is defined by a circle, the center of which corresponds to the initial contact point to be regulated and the diameter of which is in the range between $\frac{2}{3}D$ and $\frac{1}{2}D$, where D is the maximum width of the sac.

12. A blood pump according to claim 1, in which the sac is flexible and the thickness of each narrow side portion of the sac is smaller than the mean thickness of the sac, where the narrow side is defined by the side projected to a vertical plane perpendicular to the vertical plane including the maximum width of the sac.

13. A blood pump according to claim 12, in which the thickness of each narrow side portion is in the range between 20% less and 95% less than the mean thickness of the sac.

14. A blood pump according to claim 1, in which each narrow side of the sac has the nearly V-shaped cross-section at the unloaded condition so that the dihedral angle is defined by the opposite wider sides of the sac.

15. A blood pump according to claim 14, in which the dihedral angle defined by the opposite wider sides of the sac is in the range between 30° and 120° at the unloaded condition.

16. A blood pump according to claim 1, in which the inner surface contacting with the blood is coated with the material selected from the group consisting of polydimethyl siloxane, polyurethane, a block copolymer of polyurethane, a blend of polydimethyl siloxane with polyurethane, and an interpenetrating copolymer of polydimethyl siloxane and polyurethane.

17. A blood pump according to claim 1, in which at least the sac and the inlet and outlet conduits are made from polyvinyl chloride.

18. A blood pump according to claim 17, in which the mean thickness of the sac is in the range between 0.5 mm and 2.0 mm.

19. A blood pump according to claim 17, in which the material selected from the group consisting of polyurethane, polydimethyl siloxane, a blend of polyurethane and polydimethyl siloxane, a block copolymer of polyurethane and polydimethyl siloxane, and an interpenetrating copolymer of polydimethyl siloxane and polyurethane is coated to form a layer of 1–300μ thickness on the inner surface contacting with the blood.

20. A blood pump according to claim 1, in which at least the sac and the inlet and outlet conduits are made from polyurethane.

21. A blood pump according to claim 20, in which the mean thickness of the sac is in the range between 0.3 mm and 1.5 mm.

22. A blood pump according to claim 20, in which the inlet and outlet conduits are made from polyester-polyurethane and the sac is made from polyether-polyurethane of polyether origin.

23. A blood pump according to claim 1, in which at least the sac and the inlet and outlet conduits are made from polyvinyl chloride in one body.

24. A blood pump according to claim 1, in which at least the sac and the inlet and outlet conduits are made from polyurethane in one body.

* * * * *